United States Patent
Lee et al.

(10) Patent No.: US 7,947,423 B2
(45) Date of Patent: May 24, 2011

(54) PHOTOSENSITIVE COMPOUND AND PHOTORESIST COMPOSITION INCLUDING THE SAME

(75) Inventors: Jae-Woo Lee, Bucheon-Si (KR); Min-Ja Yoo, Boryeong-Si (KR); Jun-Gyeong Lee, Daejeon (KR); Young-Bae Lim, Hwaseong-Si (KR); Jae-Hyun Kim, Seoul (KR)

(73) Assignee: Dongjin Semichem Co., Ltd., Incheon (KR)

( * ) Notice: Subject to any disclaimer, the term of this patent is extended or adjusted under 35 U.S.C. 154(b) by 281 days.

(21) Appl. No.: 12/208,586

(22) Filed: Sep. 11, 2008

(65) Prior Publication Data
US 2009/0081587 A1    Mar. 26, 2009

(30) Foreign Application Priority Data
Sep. 14, 2007  (KR) ........................ 10-2007-0093374

(51) Int. Cl.
G03F 7/039    (2006.01)
G03F 7/20     (2006.01)
G03F 7/30     (2006.01)
G03F 7/38     (2006.01)
C07C 43/205   (2006.01)

(52) U.S. Cl. .................. 430/270.1; 430/325; 430/326; 430/330; 430/914; 568/643; 560/141; 560/146

(58) Field of Classification Search .......... None
See application file for complete search history.

(56) References Cited

U.S. PATENT DOCUMENTS
6,416,928 B1 *  7/2002  Ohsawa et al. ............ 430/270.1
2006/0194144 A1 *  8/2006  Sooriyakumaran et al. ......................... 430/270.1

OTHER PUBLICATIONS

Kadota et al ("Creation of Low Molecular-weight Organic Resists for Nanometer Lithography", Proceedings of SPIE—The International Society for Optical Engineering (2001), vol. 4345, p. 891-902).*
Morikawa et al ("Preparation of Poly(ether ether ketone) Dendrimers by the Divergent Method", Polymer Journal, vol. 32(3), p. 234-242 (2000)).*

* cited by examiner

*Primary Examiner* — Sin J. Lee
(74) *Attorney, Agent, or Firm* — Birch, Stewart, Kolasch & Birch, LLP

(57) ABSTRACT

A photosensitive compound whose size is smaller than conventional polymer for photoresist, and which has well-defined (uniform) structure, and a photoresist composition including the same are disclosed. The photosensitive compound represented by the following formula 1. Also, the photoresist composition comprises 1 to 85 wt % (weight %) of the photosensitive compound; 0.05 to 15 weight parts of a photo-acid generator with respect to 100 weight parts of the photosensitive compound; and 200 to 5000 weight parts of an organic solvent. In the formula 1, x is 1, 2, 3, 4 or 5, y is 2, 3, 4, 5 or 6, and R and R' are independently a chain type or a ring type of aliphatic or aromatic hydrocarbon group of 1 to 30 carbon atoms.

[Formula 1]

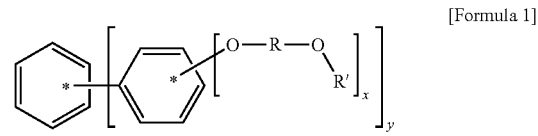

7 Claims, 1 Drawing Sheet

PHOTOSENSITIVE COMPOUND AND PHOTORESIST COMPOSITION INCLUDING THE SAME

This application claims the priority benefit of Korean Patent Application No. 10-2007-0093374 filed on Sep. 14, 2007. All disclosure of the Korean Patent application is incorporated herein by reference.

FIELD OF THE INVENTION

This invention relates to a photosensitive compound and a photoresist composition including the same. More particularly to a photosensitive compound whose size is smaller than conventional polymer for photoresist, and which has well-defined (uniform) structure, and a photoresist composition including the same

BACKGROUNDS OF THE INVENTION

The photolithography is a process used to form a circuit pattern of a semiconductor chip or a display element from a semiconductor wafer or a glass for the display element. The photoresist composition is the most essential materials to the photolithography process. So recently, as the patterns for semiconductor devices and the display elements are finer, the need for the photoresist composition having high resolution is more increased.

Conventional acid-amplified photoresist composition includes a polymer resin, a photo-acid generator (PAG), an organic solvent and a base compound as occasion demands. Since the conventional photoresist composition includes the polymer resin as a main component, it has excellent mechanical properties such as processiblity, coating stability, etching resistance and can be easily removed after the succeeding process including an etching process, an ion implantation process and so on. However, it has disadvantage in that the resolution of photoresist composition is by restricted the size of polymer resin. That is, in the photolithography process, it is impossible to form the pattern which has smaller size than the photosensitive polymer resin included in a photoresist composition. Also, as the structure of semiconductor changes to fine structure less than 65 nm, the resist which has a polymer as main component not offer uniformity for fine patterns. This is because the polymer component which is composed polymer chains of various structure, has randomicity to itself.

SUMMARY OF THE INVENTION

Therefore, it is an object of the present invention to provide a photosensitive compound whose size is smaller than conventional polymer for photoresist, and which has well-defined (uniform) structure, and a photoresist composition including the same. It is another object of the present invention to provide a photosensitive compound which can improve resolution of lithography process, and has advanced line edge roughness (LER), and can improve uniformity of layer after coating or forming pattern, and a photoresist composition including the same. It is still another object of the present invention to provide a photosensitive compound has excellent dry etch resistance, and can reduce the formation of a scum, and a photoresist composition including the same.

In order to achieve these objects, the present invention provides a photosensitive compound represented by the following Formula 1,

[Formula 1]

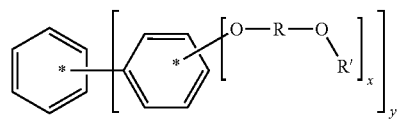

In the Formula 1, x is 1, 2, 3, 4 or 5, y is 2, 3, 4, 5 or 6, and R and R' are independently a chain type or a ring type of aliphatic or aromatic hydrocarbon group of 1 to 30 carbon atoms.

The present invention also provides a photoresist composition comprising 1 to 85 wt % (weight %) of the photosensitive compound; 0.05 to 15 weight parts of a photo-acid generator with respect to 100 weight parts of the photosensitive compound; and 200 to 5000 weight parts of an organic solvent. The present invention also provides a method for forming photoresist pattern composition comprising the step of: (a) coating a photoresist composition on a substrate to form a photoresist layer; (b) exposing the photoresist layer to a light; (c) heating the exposed photoresist layer; and (d) developing the heated photoresist layer to form the photoresist pattern.

DETAILED DESCRIPTION OF THE INVENTION

Figure 1:
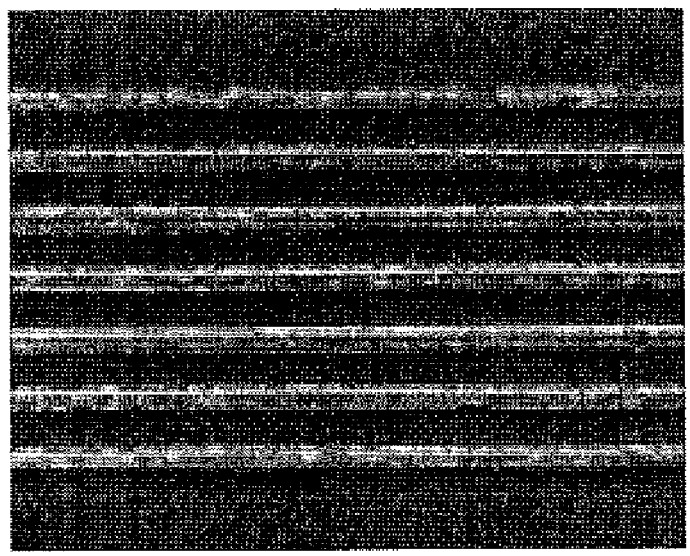
FIG. 1 shows an electron microphotograph of the photoresist pattern formed by using a photoresist composition according to one embodiment of the present invention.

A more complete appreciation of the invention, and many of the attendant advantages thereof, will be better appreciated by reference to the following detailed description.

The photosensitive compound according to the present invention has a structure which can be deprotected by an acid, and is represented by the following Formula 1.

[Formula 1]

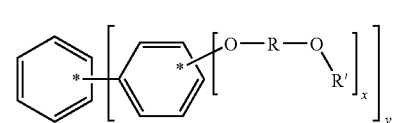

In the Formula 1, x is 1, 2, 3, 4 or 5, y is 2, 3, 4, 5 or 6, and R and R' are independently a chain type or a ring type of aliphatic or aromatic hydrocarbon group of 1 to 30, preferably, 2 to 20 carbon atoms, if necessary, the R and R' can comprise a substituents such as a carbonyl group, a phenyl group, a sulfonyl group, a fluoroalkyl group, or 1 to 8 heteroatoms, preferably, carbonyl(C=O) groups are positioned at the both ends of the R, and the R' can include an ether compound structure which includes oxygen (O) atom.

The representative examples of the photosensitive compound represented by the Formula 1 include compounds represented by the following Formulas 2 to 4.

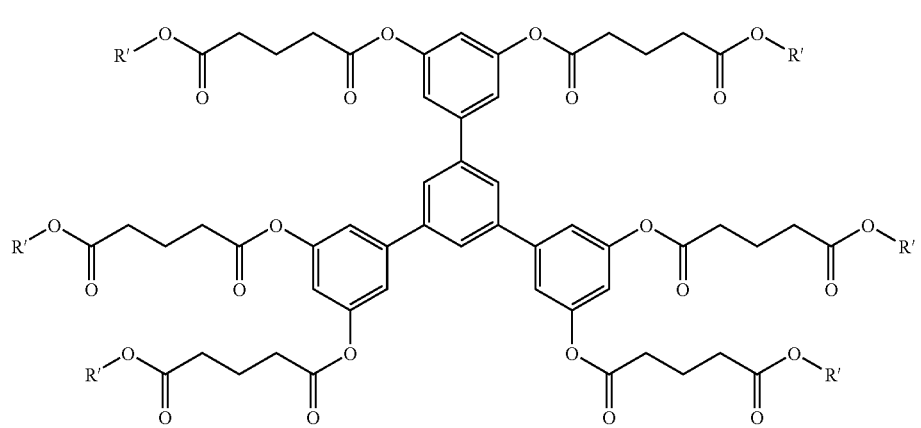
[Formula 2]
In the Formula 2, R' is independently
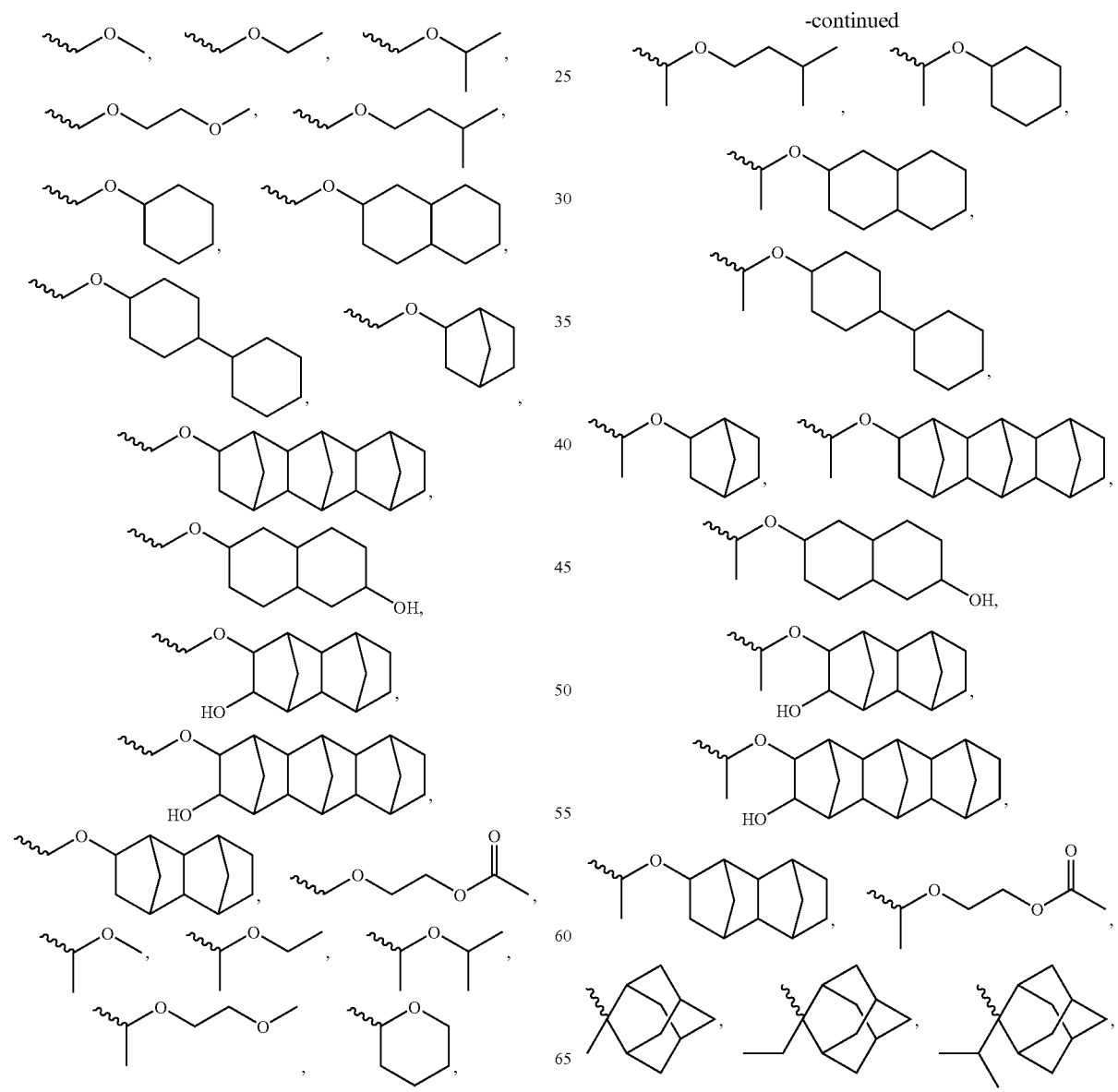

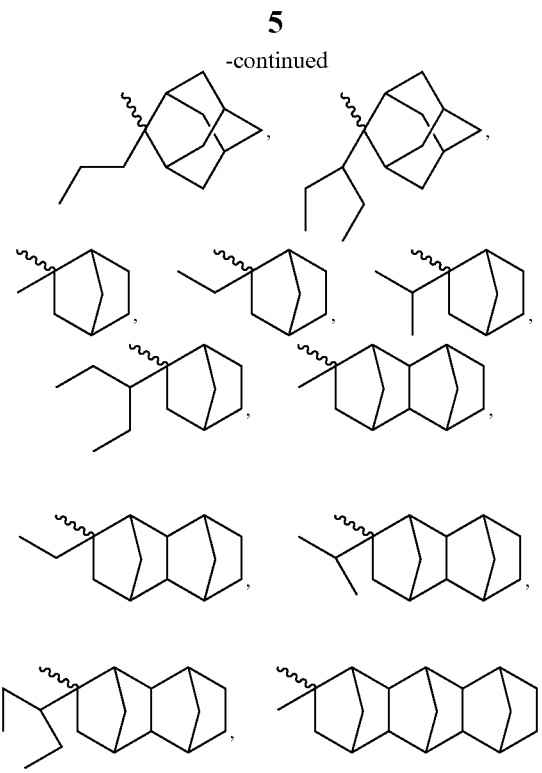
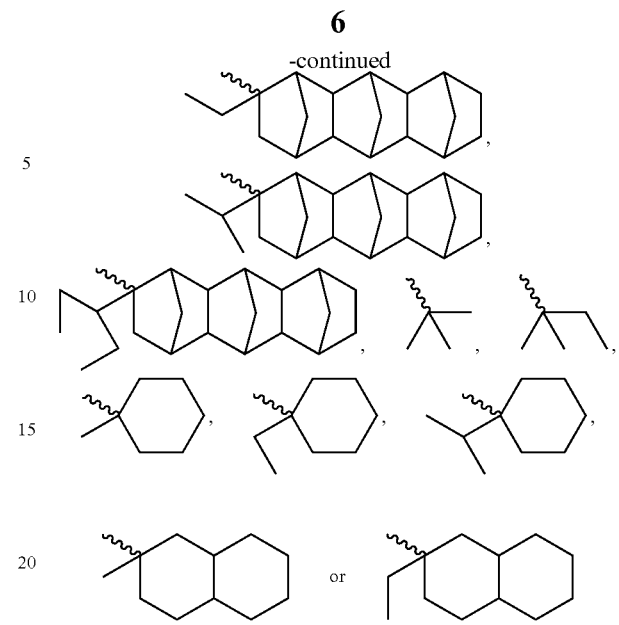
(wherein, the meandering line indicates a bonding part).
The representative examples of the photosensitive compound represented by the Formula 2 include compounds represented by the following Formulas 2a to 2d.
[Formula 2a]
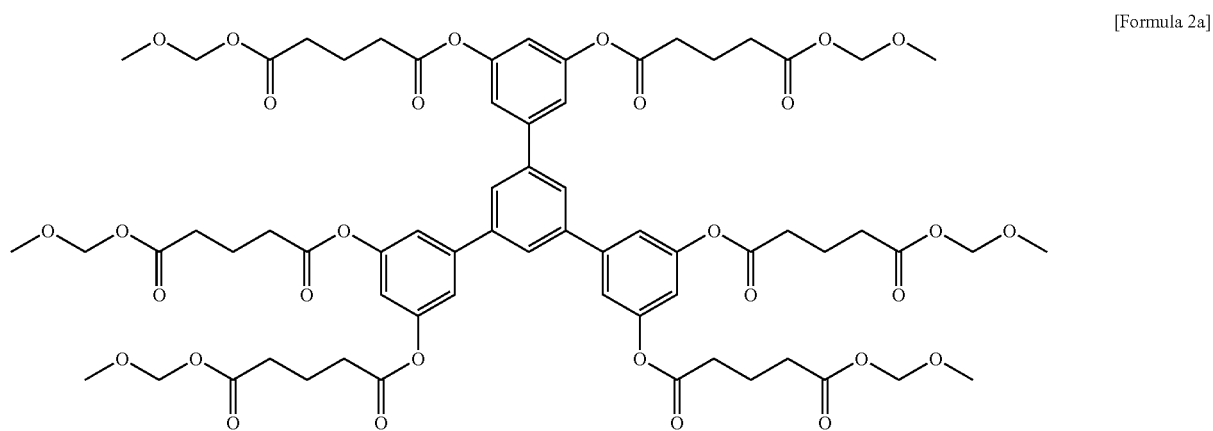
[Formula 2b]
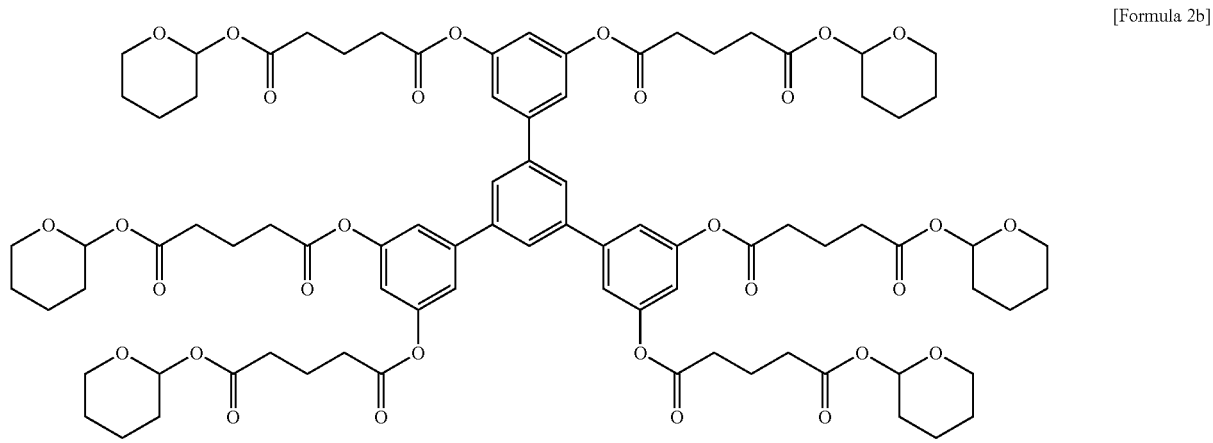

-continued
[Formula 2c]
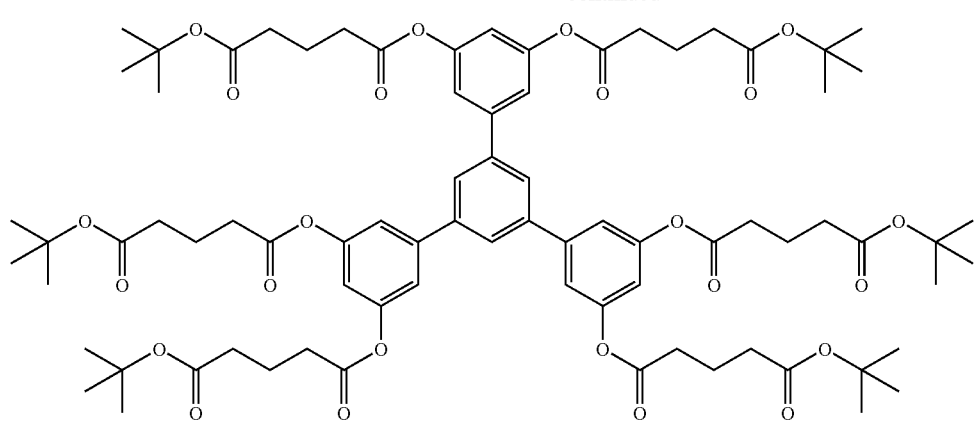
[Formula 2d]
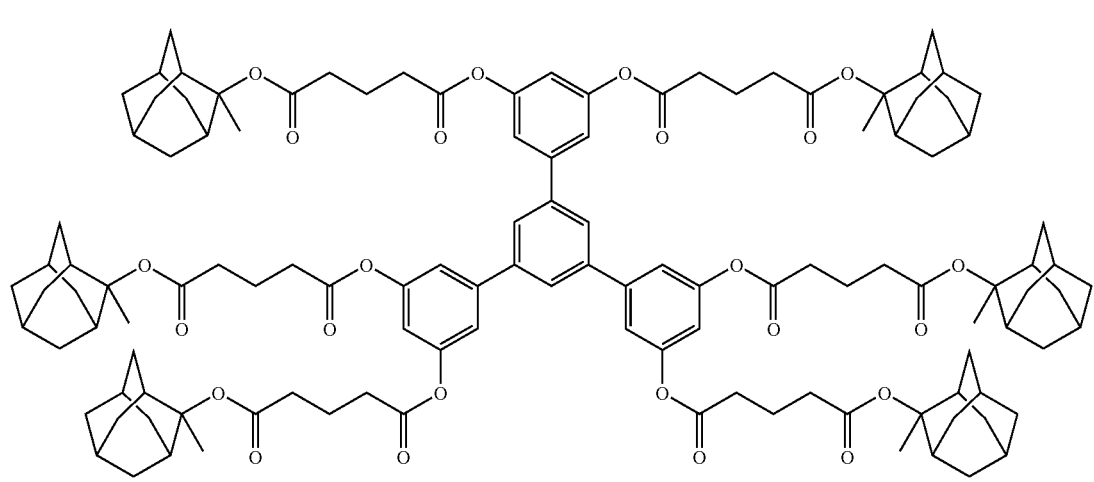
[Formula 3]
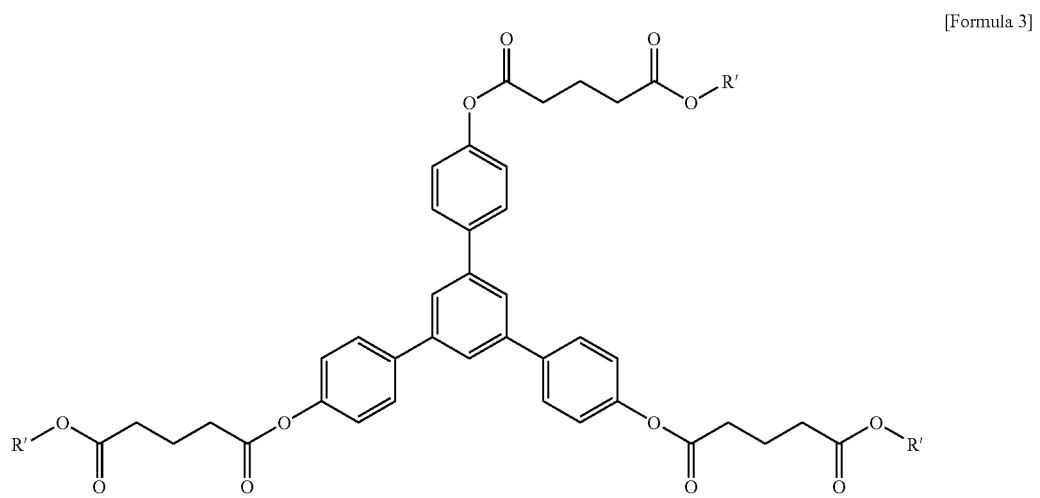
In the Formula 3, R' is the same as defined in the Formula 2. The representative examples of the photosensitive compound represented by the Formula 3 include compounds represented by the following Formulas 3a to 3d.

[Formula 3a]
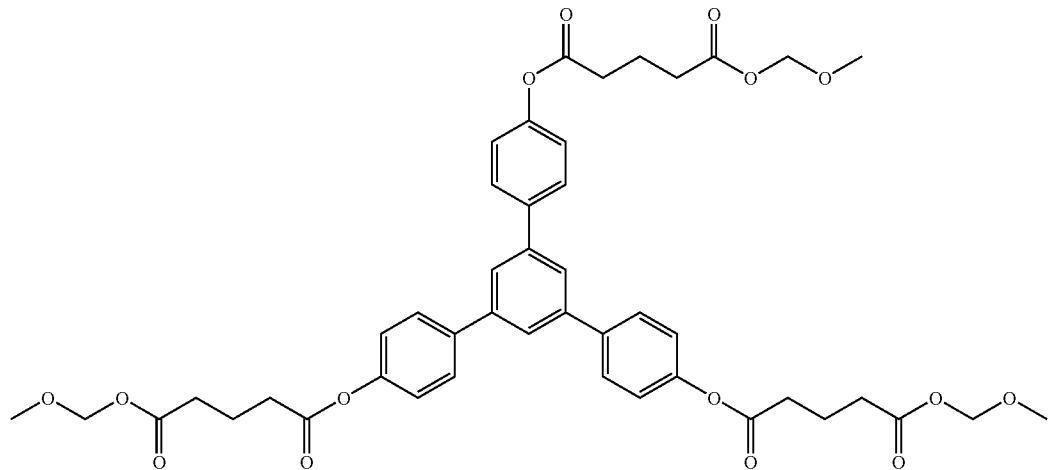
[Formula 3b]
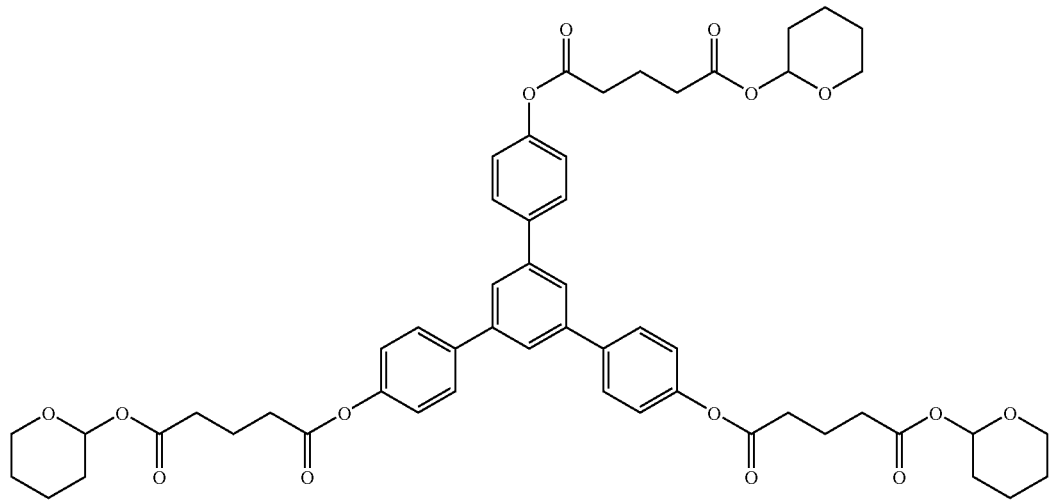
[Formula 3c]
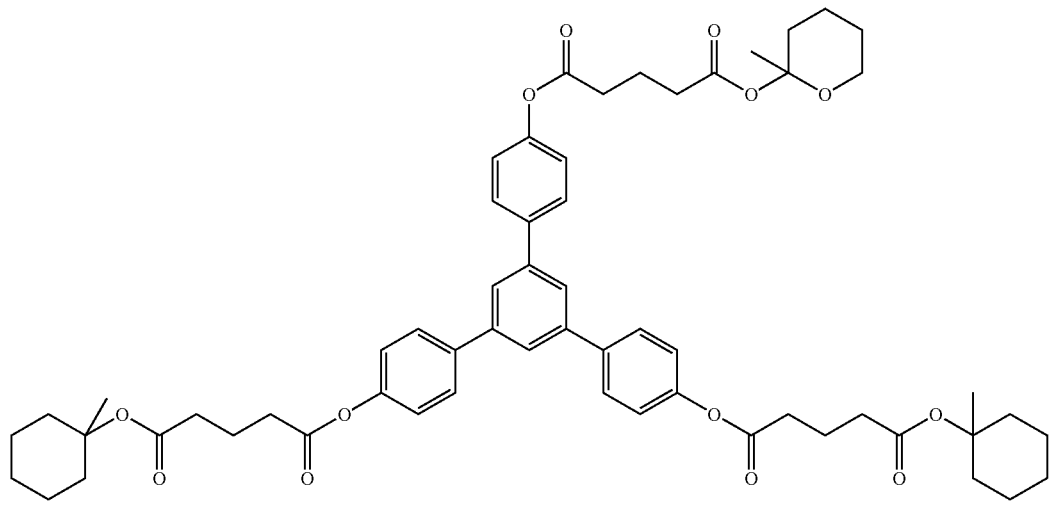

[Formula 3d]
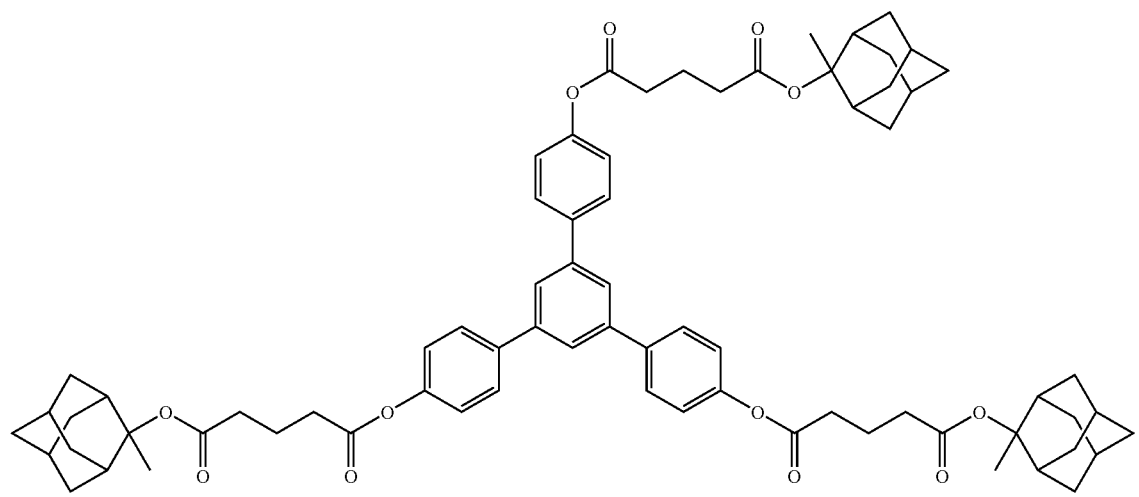
[Formula 4]
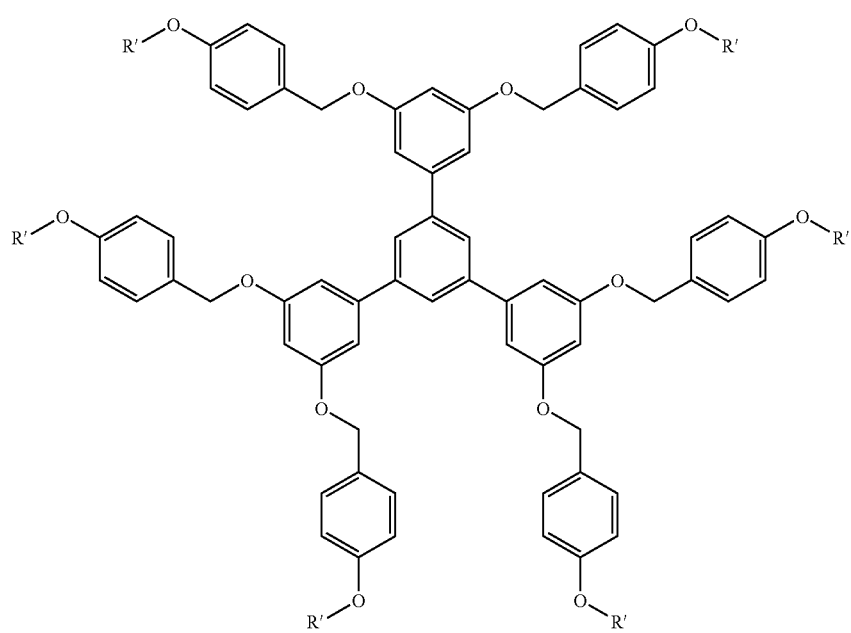
In the Formula 4, R' is the same as defined in the Formula 2. The representative examples of the photosensitive compound represented by the Formula 4 include compounds represented by the following Formulas 4a to 4c.

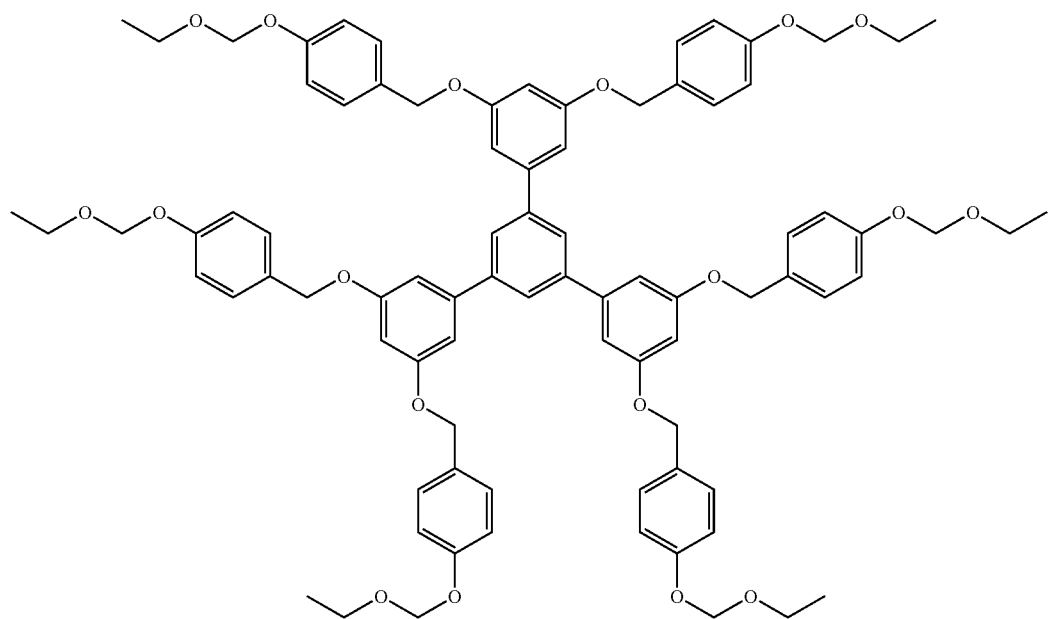
[Formula 4a]
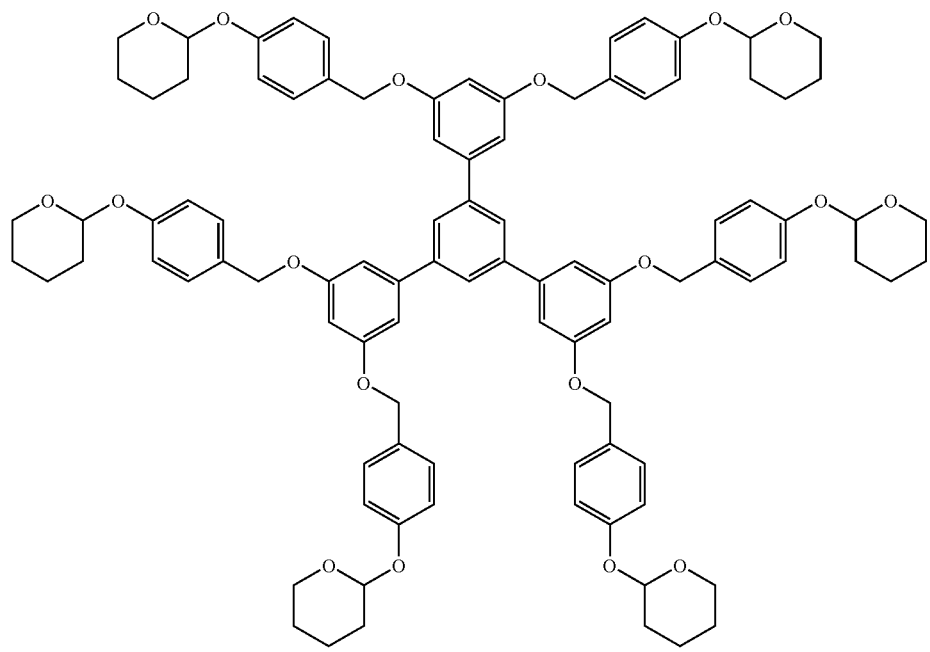
[Formula 4b]

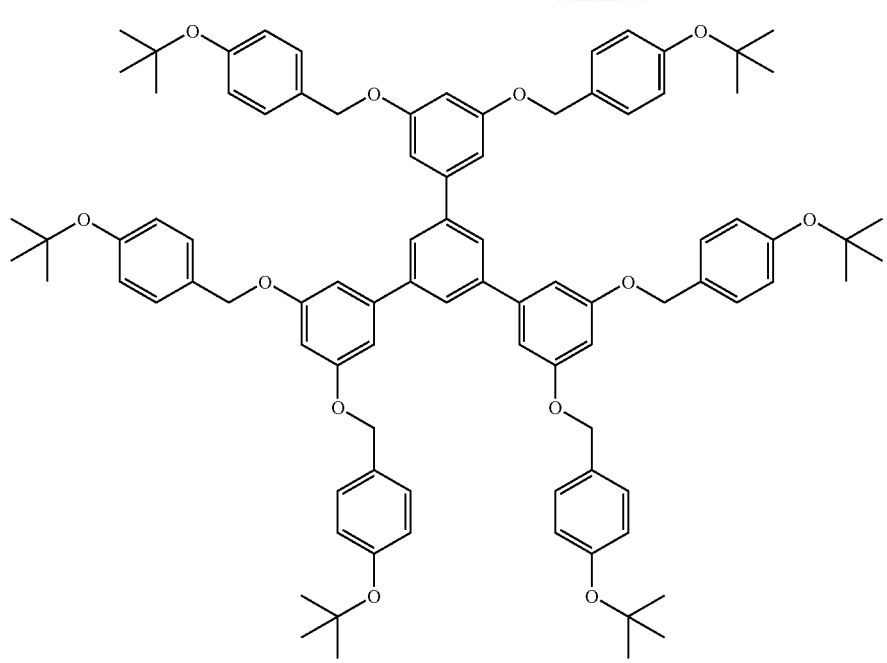

[Formula 4c]

The photosensitive compound represented by the Formula 1 can be synthesized by conventional organic synthesis methods. For example, an intermediate is synthesized by a condensation reaction of acetophenone derivatives as described in the following Reaction 1 (Wherein, n is an integer of 1 to 5 independently).

[Reaction 1]

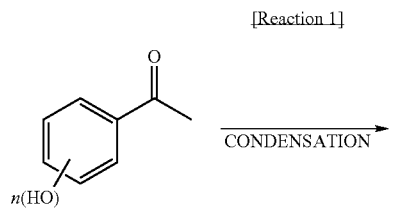

[Reaction 2]

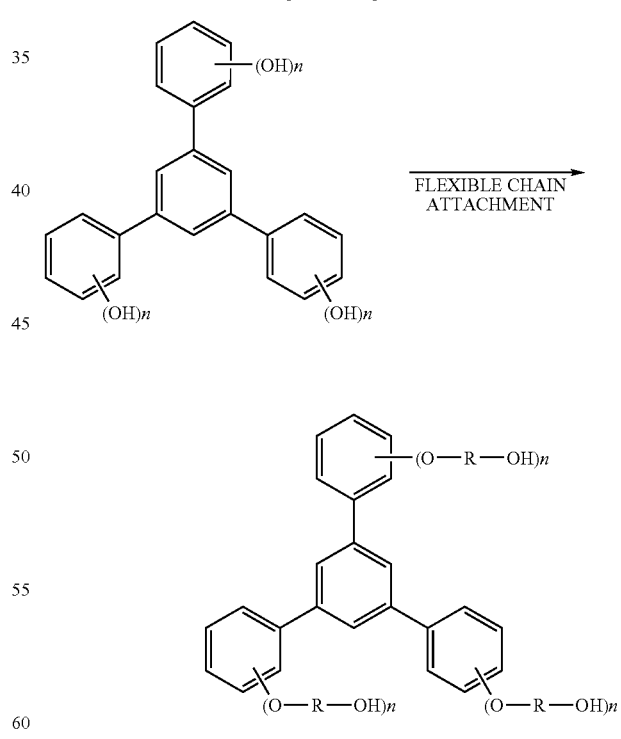

Thereafter, the bonding reaction between a hydroxyl group of synthesized intermediate and a flexible linear functional group (—ROH) is occurred, as described in the following Reaction 2 (Wherein, n is an integer of 1 to 5 independently, and R is the same as defined in the Formula 1).

Thereafter, the photosensitive compound according to the present invention is synthesized by protecting hydroxyl group of the end of flexible chain type functional group (—ROH) with R', as described in the following Reaction 3 (Wherein, n is an integer of 1 to 5 independently, and R and R' are the same as defined in the Formula 1).

[Reaction 3]

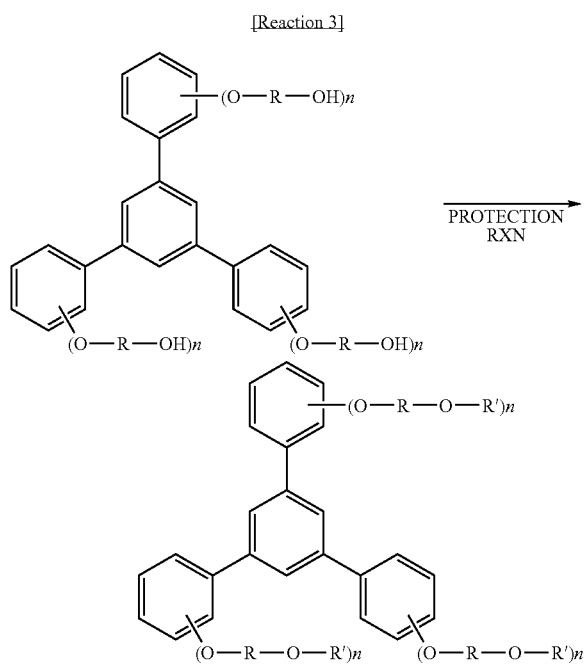

The photosensitive compound according to the present invention has more well-defined (uniform) structure because the photosensitive compound has a smaller size than a conventional polymer for photoresist, and has a uniform size and structure. Besides, the acid formed by photo-acid generator under exposing process, deprotects the dissolution inhibitor protecting group acid so that the solubility in developer is increased to selectively develop only the exposed region.

The photoresist composition according to the present invention includes the photosensitive compound represented by the Formula 1, a photo-acid generator and an organic solvent, and, if necessary, further includes a base compound as a quencher, and a surfactant. In the photoresist composition, the amount of the photosensitive compound is 1 to 85 wt % (weight %), preferably 10 to 45 wt %, the amount of the photo-acid generator is 0.05 to 15 weight parts, preferably 0.15 to 5.5 weight parts with respect to 100 weight parts of the photosensitive compound, and the amount of the organic solvent is 200 to 5000 weight parts. Also, the amount of the base compound, if used, is 0.01 to 10 weight parts, preferably 1 to 2 weight parts with respect to 100 weight parts of the photosensitive compound. Wherein, if the amount of the photosensitive compound is too little (less than 1 wt %), it is difficult to form the photoresist layer with a desired thickness. If the amount of the photosensitive compound is too much (more than 85 wt %), the thickness of patterns formed on the wafer may be not uniform. Also, if the amount of the PAG (photo-acid generator) is too little (less than 0.05 weight parts), the light sensitivity of the photoresist composition may decrease. if the amount of the PAG is too much (more than 15 weight parts), the profile of the photoresist patterns may be deteriorated because the PAG absorbs a lot of ultraviolet rays and a large quantity of acid is produced from the PAG. Also, if the amount of the base compound is too little (less than 0.01 weight parts), it is not easy to control a diffusion of the acid generated in an exposure process so that the pattern profile is uneven. If the amount of the base compound is too much (more than 10 weight parts), the diffusion of the acid generated is suppressed so that pattern is not easily formed.

As the PAG (photo-acid generator), any conventional PAG which can generate an acid when exposed to a light, can be used. The non-limiting examples of the PAG include onium salts such as sulfonium salts or iodonium salts. Specifically, the PAG is selected from a group consisting of phthalimidotrifluoromethane sulfonate, dinitrobenzyltosylate, n-decyl disulfone and naphthylimido trifluoromethane sulfonate. Also, the PAG is selected from the group consisting of diphenyl iodonium triflate, diphenyl iodonium nonaflate, diphenyl iodonium hexafluorophosphate, diphenyl iodonium hexafluoroarsenate, diphenyl iodonium hexafluoroantimonate, diphenyl p-methoxyphenyl sulfonium triflate, diphenyl p-toluenyl sulfonium triflate, diphenyl p-tert-butylphenyl sulfonium triflate, diphenyl p-isobutylphenyl sulfonium triflate, triphenylsulfonium triflate, tris(p-tert-butylphenyl) sulfonium triflate, diphenyl p-methoxyphenyl sulfonium nonaflate, diphenyl p-toluenyl sulfonium nonaflate, diphenyl p-tert-butylphenyl sulfonium nonaflate, diphenyl p-isobutylphenyl sulfonium nonaflate, triphenylsulfonium nonaflate, tris(p-tert-butylphenyl) sulfonium nonaflate, triphenylsulfonium hexafluoroarsenate, triphenylsulfonium hexafluoroantimonate, triphenylsulfonium triflate and dibutylnaphtylsulfonium triflate.

As the organic solvent, the conventional various organic solvents for the photoresist composition can be used. Exemplary organic solvents include, but are not limited to, ethyleneglycol monomethylethyl, ethyleneglycol monoethylether, ethyleneglycol monomethylether, ethyleneglycol monoacetate, diethylene glycol, diethyleneglycol monoethylether, propyleneglycol monomethyletheracetate (PGMEA), propyleneglycol, propyleneglycol monoacetate, toluene, xylene, methylethylketone, methyl isoamyl ketone, cyclohexanone, dioxane, methyl lactate, ethyl lactate, methyl pyruvate, ethyl pyruvate, methyl methoxy propionate, ethyl ethoxy propionate, N,N-dimethylformamide, N,N-dimethylacetamide, N-methyl-2-pyrollidone, 3-ethoxy ethyl propionate, 2-heptanone, γ-butyrolactone, ethyl 2-hydroxy propionate, ethyl 2-hydroxy-2-methyl propionate, ethoxyethyl acetate, hydroxylethyl acetate, methyl 2-hydroxy-3-methylbutanoate, methyl 3-methoxy-2-methylpropionate, ethyl 3-ethoxy propionate, ethyl 3-methoxy-2-methyl propionate, ethyl acetate, butyl acetate, and mixture thereof.

Also, as the base compound which is used as quencher or reaction inhibitor, the conventional quenchers or reaction inhibitors, for example, organic bases such as tri-ethylamine, trioctylamine, tri-iso-butylamine, tri-iso-octylamine, di-ethanolamine, tri-ethanolamine and mixture thereof, can be used without limitation. The surfactant, at need, is added in the present photoresist composition so as to improve a mixing uniformity of the photoresist composition, coating property of the photoresist composition and developing property of the photoresist film after the light exposure. As the surfactant, conventional various surfactant as the photoresist composition can be used. Exemplary surfactants include, but are not limited to, fluorine-based surfactant or fluorine-silicon-based surfactant. The amount of the surfactant is 0.001 to 2 weight parts, preferably 0.01 to 1 weight parts with respect to solid content 100 weight parts of the photoresist composition. If the amount of the surfactant is too little, function of surfactant does not sufficiently work, and if the amount of the surfactant is too much, the resist property such as shape stability or a storage stability of the composition except for the coating property, may be adversely affected. Also, if necessary, as the photosensitive polymer according to the present invention, conventional photosensitive polymer for the photoresist, which reacts with an acid and its solubility to a developer is changed within the limits not to interfere the role of the light sensitive compound, can be used. The photosensitive polymer may be block copolymer or random copolymer having acid sensitive protecting group, and the weight average molecular weight (Mw) of photosensitive polymer is preferably 3,000 to 20,000.

In order to form a photoresist pattern with the photoresist composition according to the present invention, the following conventional photolithography process can be carried out. First, the photoresist is applied or coated on a substrate such as silicon wafer, an aluminum substrate, and so on, for example, with a spin coater to form a photoresist layer. The photoresist layer is exposed to a light of a predetermined pattern. After the exposure, if necessary, the photoresist pattern is thermally treated (heated), which is called as PEB (Post Exposure Bake), and is developed to form the photoresist pattern. As the developing solution for the developing process, an alkali aqueous solution including an alkali compound such as sodium hydroxide, potassium hydroxide, sodium carbonate, tetramethylammonium hydroxide (TMAH) of the concentration of 0.1 to 10 weight % can be used. If necessary, the developing solution may further include water-soluble organic solvent such as methanol, ethanol, and a surfactant of a proper amount.

Hereinafter, the preferable examples are provided for better understanding of the present invention. However, the present invention is not limited by the following examples.

SYNTHESIS EXAMPLE 1

Preparation of Photosensitive Compound Represented by the Formula 2a (A) As shown in the following Reaction 4, 0.1 mol (15.2 g) of 3,5-dihydroxy acetophenone and 200 ml of tetrahydrofuran (THF) of solvent were added into a 500 ml 2-neck round reaction flask and stirred. After purging dry nitrogen for 30 minutes to completely remove air, the reaction flask was put in the iced water. Leaving the reaction flask in the iced water for 30 minutes, temperature of reactant was maintained at 0□ and hydrogen chloride gas was bubbled for 90 minutes. Thereafter the reaction was carried out for 12 hours at room temperature. After completion of the reaction, the solvent was removed under the reduced pressure to obtain an intermediate of photosensitive compound (Yield: 45%) ($^1$H-NMR: s(7.66, 3H), s(6.51, 6H), s(6.16, 3H), br(5.2, 6H)).

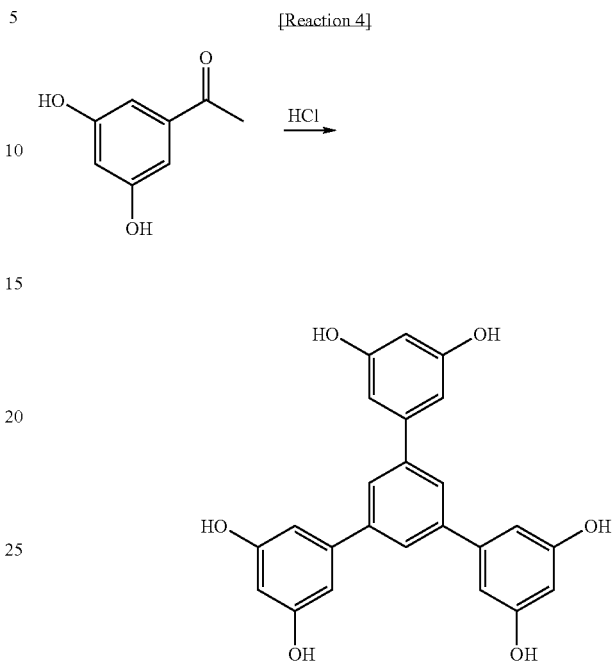

[Reaction 4]

(B) 0.01 mol (4.02 g) of the intermediate obtained above process and 0.065 mol (7.41 g) of glutaric anhydride were added into 250 ml round flask and 150 ml of toluene was further added to dissolve the intermediate and glutaric anhydride. Thereafter, the reflux reaction was carried out for 12 hours while stirring the reactant under the nitrogen atmosphere. After the completion of the reaction, the solvent was removed and the white-powdered photosensitive compound represented by the following Formula 5 was obtained without additional refining process (Yield: 75%) ($^1$H-NMR: s(7.66, 3H), s(7.1, 6H), s(6.84, 3H), m(2.23, 24H), m(1.83, 12H), br(10.8, 6H)).

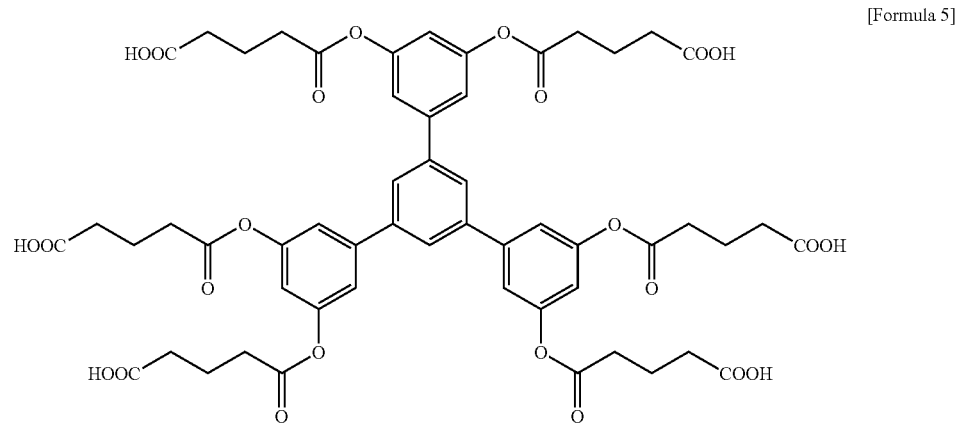

[Formula 5]

(c) 0.01 mol (10.9 g) of the intermediate represented by the Formula 5 and 250 ml of tetrahydrofuran (THF) of solvent were added into a 500 ml 2-neck round reaction flask and stirred. Thereafter, under the dry nitrogen atmosphere, 20% THF solution of 0.012 mol (0.54 g) of methoxymethyl chloride was added, and the reaction was carried out for 12 hours at room temperature. After the completion of the reaction, the solvent was removed under the reduced pressure and 11.5 g of the photosensitive compound represented by the Formula 2a was obtained (Yield: 85%) ($^1$H-NMR: s(7.7, 3H), s(7.1, 6H), s(6.79, 3H), s(6.2, 12H), s(3.3, 18H), m(2.1, 36H)).

SYNTHESIS EXAMPLE 2

Preparation of Photosensitive Compound Represented by the Formula 2b

Except for using 0.012 mol (1.0 g) of 3,4-dihydro-2H-pyran instead of 0.012 mol (0.54 g) of methoxymethyl chloride, 10.3 g of the photosensitive compound represented by the Formula 2b was obtained according to the same manner of Synthesis Example 1 (Yield: 65%) ($^1$H-NMR: s(7.7, 3H), s(7.1, 6H), s(6.79, 3H), s(6.1, 6H), s(3.6, 12H), m(2.1, 36H), m(1.7, 36H)).

SYNTHESIS EXAMPLE 3

Preparation of Photosensitive Compound Represented by the Formula 2c

Except for using 0.012 mol (0.68 g) of tert-butanol instead of 0.012 mol (0.54 g) of methoxymethyl chloride, and except for carrying out 12 hours-reflux reaction in Dean-Stark apparatus, 7.1 g of the photosensitive compound represented by the Formula 2c was obtained according to the same manner of Synthesis Example 1 (Yield: 50%) ($^1$H-NMR: s(7.7, 3H), s(7.1, 6H), s(6.79, 3H), m(2.1, 36H), s(1.4, 54H)).

SYNTHESIS EXAMPLE 4

Preparation of Photosensitive Compound Represented by the Formula 2d

Except for using 0.012 mol (2.1 g) of 2-methyl-2-adamantanol instead of 0.012 mol (0.54 g) of methoxymethyl chloride, and except for carrying out 12 hours-reflux reaction in Dean-Stark apparatus, 8.9 g of the photosensitive compound represented by the Formula 2d was obtained according to the same manner of Synthesis Example 1 (Yield: 45%) ($^1$H-NMR: s(7.7, 3H), s(7.1, 6H), s(6.79, 3H), m(2.7, 12H), m(2.1, 36H), m(1.4, 90H)).

SYNTHESIS EXAMPLE 5

Preparation of Photosensitive Compound Represented by the Formula 3a (A) 0.1 mol (13.6 g) of 4-hydroxy acetophenone and 200 ml of tetrahydrofuran (THF) of solvent were added into a 500 ml 2-neck round reaction flask and stirred. After purging dry nitrogen for 30 minutes to completely remove air, the reaction flask was put in the iced water. Leaving the reaction flask in the iced water for 30 minutes, temperature of reactant was maintained at 0° C. and hydrogen chloride gas was bubbled for 90 minutes. Thereafter the reaction was carried out for 12 hours at room temperature. After completion of the reaction, the solvent was removed under the reduced pressure to obtain the intermediate of photosensitive compound represented by the Formula 3a (Yield: 55%) ($^1$H-NMR: s(7.6, 3H), s(7.31, 6H), s(6.79, 6H), br(5.0, 3H)).

(B) 0.01 mol (3.54 g) of the intermediate obtained above process and 0.065 mol (7.41 g) of glutaric anhydride were added into 250 ml round flask and 150 ml of toluene was further added to dissolve the intermediate and glutaric anhydride. Thereafter, the reflux reaction was carried out for 12 hours while stirring the reactant under the nitrogen atmosphere. After the completion of the reaction, the solvent was removed and the white-powdered intermediate of photosensitive compound represented by the following Formula 6 was obtained without additional refining process (Yield: 78%) ($^1$H-NMR: s(7.66, 3H), s(7.45, 6H), s(7.13, 6H), m(2.23, 12H), m(1.83, 6H), br(11, 3H)).

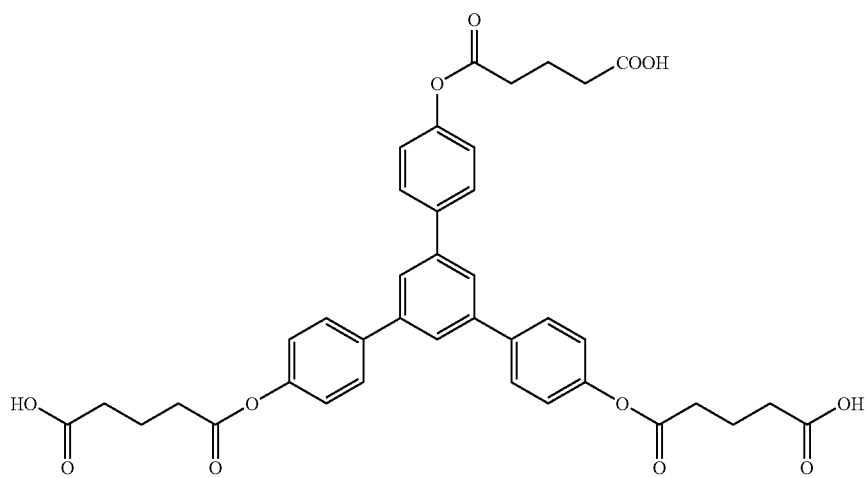

[Formula 6]

(c) 0.01 mol (7.0 g) of the intermediate represented by the Formula 6 and 250 ml of tetrahydrofuran (THF) of solvent were added into a 500 ml 2-neck round reaction flask and stirred. Thereafter, under the dry nitrogen atmosphere, 20% THF solution of 0.012 mol (0.54 g) of methoxymethyl chloride was added, and the reaction was carried out for 12 hours at room temperature. After the completion of the reaction, the solvent was removed under the reduced pressure and 7.5 g of the photosensitive compound represented by the Formula 3a was obtained (Yield: 95%) ($^1$H-NMR: s(7.7, 3H), s(7.5, 6H), s(7.1, 6H), s(6.2, 6H), s(3.2, 9H), t(2.2, 12H), m(1.9, 6H)).

SYNTHESIS EXAMPLE 6

Preparation of Photosensitive Compound Represented by the Formula 3b

Except for using 0.012 mol (1.0 g) of 3,4-dihydro-2H-pyran instead of 0.012 mol (0.54 g) of methoxymethyl chloride, 6.6 g of the photosensitive compound represented by the Formula 3b was obtained according to the same manner of Synthesis Example 5 (Yield: 70%) ($^1$H-NMR: s(7.7, 3H), s(7.5, 6H), s(7.1, 6H), t(6.1, 3H), t(3.6, 6H), t(2.2, 12H), m(1.9, 12H), m(1.6, 12H)).

SYNTHESIS EXAMPLE 7

Preparation of Photosensitive Compound Represented by the Formula 3c

Except for using 0.012 mol (1.4 g) of 1-methyl-1-cyclohexanol instead of 0.012 mol (0.54 g) of methoxymethyl chloride, and except for carrying out 12 hours-reflux reaction in Dean-Stark apparatus, 4.9 g of the photosensitive compound represented by the Formula 3c was obtained according to the same manner of Synthesis Example 5 (Yield: 50%) ($^1$H-NMR: s(7.7, 3H), s(7.5, 6H), s(7.1, 6H), t(2.2, 12H), m(1.9, 6H), m(1.6, 12H), m(1.45, 27H)).

SYNTHESIS EXAMPLE 8

Preparation of Photosensitive Compound Represented by the Formula 4a (A) The condensation reaction of 3,5-dihydroxy acetophenone was carried out in the same manner as described in Synthesis Example 1 to obtain an intermediate of the photosensitive compound represented by Reaction 4.

(B) 0.01 mol (4.02 g) of the intermediate obtained in this example and 0.065 mol (14.0 g) of 4-bromomethyl-benzoic acid were added into 250 ml round flask and 150 ml of THF was further added to dissolve the intermediate and 4-bromomethyl-benzoic acid. Thereafter, the reflux reaction was carried out for 12 hours while stirring the reactant under the nitrogen atmosphere. After the completion of the reaction, the resultant was refined through column chromatography method (solvent: ethylacetate/methanol=9/1), to obtain the white-powdered photosensitive compound represented by the following Formula 7 (Yield: 55%) ($^1$H-NMR: s(8.06, 12H), s(7.66, 3H), s(7.4, 12H), s(6.45, 6H), s(6.24, 3H), s(5.2, 12H), br(10.8, 6H)).

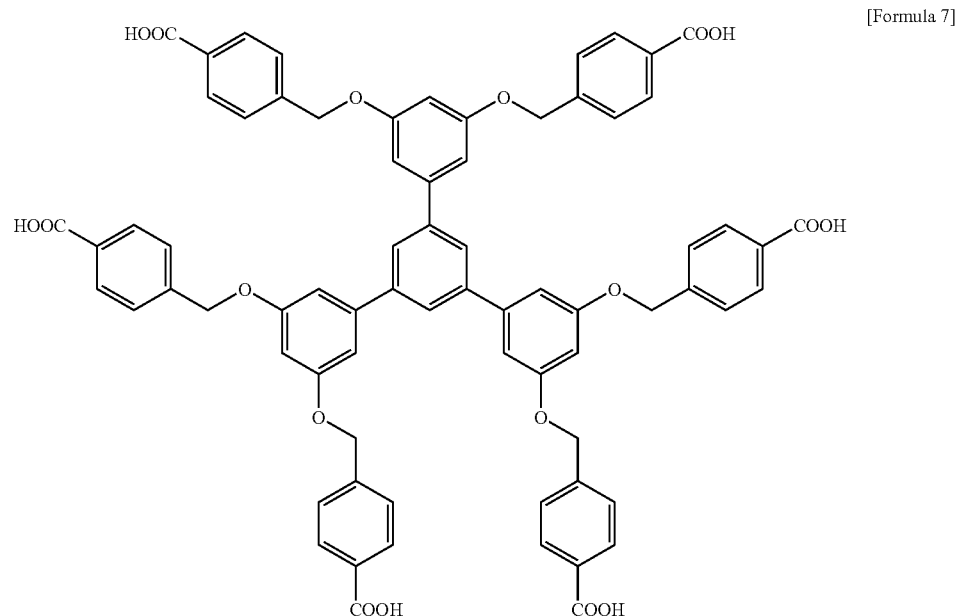

[Formula 7]

(c) 0.01 mol (11.3 g) of the intermediate represented by the Formula 7 and 250 ml of tetrahydrofuran (THF) of solvent were added into a 500 ml 2-neck round reaction flask and stirred. Thereafter, under the dry nitrogen atmosphere, 20% THF solution of 0.012 mol (0.54 g) of methoxymethyl chloride was added, and the reaction was carried out for 12 hours at room temperature. After the completion of the reaction, the solvent was removed under the reduced pressure and 11.0 g of the photosensitive compound represented by the Formula 4a was obtained (Yield: 80%) ($^1$H-NMR: s(7.6, 3H), s(7.1, 6H), s(6.7, 6H), s(6.5, 6H), s(6.2, 3H), s(6.0, 12H), s(5.2, 12H), q(3.4, 12H), t(1.1, 18H)).

EXAMPLES 1 to 8

Preparation of Photoresist Composition and Formation of Photoresist Pattern Using the Photoresist Composition The photosensitive compound in the following Table 1, 400 weight parts of PGMEA as an organic solvent with respect to 100 weight parts of the photosensitive compound in Table 1, 4.5 weight parts of triphenylsulfonium nonaflate as a PAG with respect to 100 weight parts of the photosensitive compound in Table 1 and 2 weight parts of trioctylamine as a resist quencher with respect to 100 weight parts of the photosensitive compound in Table 1 were mixed. The mixture was stirred for 4 hours at room temperature and filtrated to manufacture a photoresist composition.

TABLE 1

| | Photosensitive compound |
|---|---|
| Example 1 | The compound of Formula 2a, 25 g |
| Example 2 | The compound of Formula 2b, 25 g |
| Example 3 | The compound of Formula 2c, 25 g |
| Example 4 | The compound of Formula 2d, 25 g |
| Example 5 | The compound of Formula 3a, 25 g |
| Example 6 | The compound of Formula 3b, 25 g |
| Example 7 | The compound of Formula 3c, 25 g |
| Example 8 | The compound of Formula 4a, 25 g |

The photoresist composition manufactured was spin-coated by 3000 Å on a silicon wafer to form a photoresist thin film. Then the photoresist thin film was soft-baked in an oven or heat fan at 130° C. for 90 seconds and then exposed by EUVL (extreme ultraviolet lithography) instrument. Thereafter, the photoresist thin film was again baked at 130° C. for 90 seconds. The baked wafer was dipped in 2.38 wt % TMAH (trimethyl ammonium hydroxide) aqueous solution for 40 seconds for developing to form 32 nm L/S (line/space) pattern. The features of the formed photoresist pattern were measured and the results are shown in the following Table 2. The electron microphotograph of the photoresist pattern according to Example 1 is shown in FIG. 1.

TABLE 2

| | Resolution | LER | Coating uniformity | Etching resistance to novolac resin | Scum control | Profile |
|---|---|---|---|---|---|---|
| Example 1 | <32 nm | 1.1 nm | 2.2% | 93% | Free | Rectangular |
| Example 2 | <32 nm | 2.0 nm | 3.2% | 95% | Free | Rectangular |
| Example 3 | <32 nm | 2.3 nm | 2.9% | 100% | Free | Rectangular |
| Example 4 | <32 nm | 1.6 nm | 2.7% | 87% | Free | Rectangular |
| Example 5 | <32 nm | 2.4 nm | 2.7% | 81% | Free | Rectangular |
| Example 6 | <32 nm | 2.5 nm | 2.5% | 85% | Free | Rectangular |
| Example 7 | <32 nm | 3.0 nm | 2.5% | 98% | Free | Rectangular |
| Example 8 | <32 nm | 2.9 nm | 2.5% | 105% | Free | Rectangular |

In Table 2, the coating uniformity was measured by Nanospec instrument, and the etching resistance is the thickness variation after a dry etching and was measured by Nanospec instrument. Scum and profile were observed by a naked eye. From Table 2, the photosensitive compound and the photoresist composition including the same of the present invention enable the minimum and uniform pattern formation so that the resolution of the lithography process of less than 32 nm can be made and also line edge roughness (LER) of less than 3 nm (3 sigma) can be controlled. Also, the photoresist composition of the present invention has advantages of excellent coating uniformity in that non-uniformity of the coating film is less than 3%, dry etching resistance which is as good as novolac resin, and low scum generation.

In the photoresist composition of the present invention, the minimum resolution of the lithography process can be improved less than 32 nm by promoting the resolution of the photoresist by minimizing the dimension of constructing unit of the photosensitive layer. Also, a constructing unit for forming the photoresist pattern is small sized and is of simple pure material so that semi-conductive property can be insured by controlling LER less than 3 mm. The attraction between constructing units is uniform so that the coating uniformity can be remained within 3%. Besides, in the photoresist composition according to the present invention, the amount of benzene rings in the molecule composing the photosensitive layer is high so that dry etching resistance is enhanced similarly to novolac resin and the generation of abnormal pattern after development, that is scum, can be inhibited sufficiently. The scum is caused by components insoluble to the developer and causes uneven etching.

The invention claimed is:

1. A photosensitive compound having a structure of the following Formula 1,

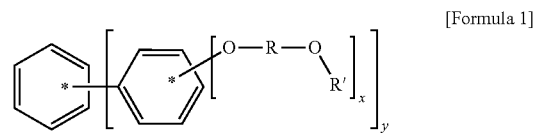

[Formula 1]

wherein, x is 1, 2, 3, 4 or 5, y is 2, 3, 4, 5 or 6, R and R' are independently a chain type or ring type of an aliphatic or aromatic hydrocarbon group of 1 to 30 carbon atoms, wherein (A) carbonyl (C=O) groups are positioned at both ends of R; or (B) R comprises an unsubstituted phenyl group.

2. The photosensitive compound of claim 1, wherein, carbonyl (C=O) groups are positioned at the both ends of the R.

3. The photosensitive compound of claim 1, wherein the photosensitive compound is selected from a group consisting of compounds represented by the following Formulas 2 to 4,

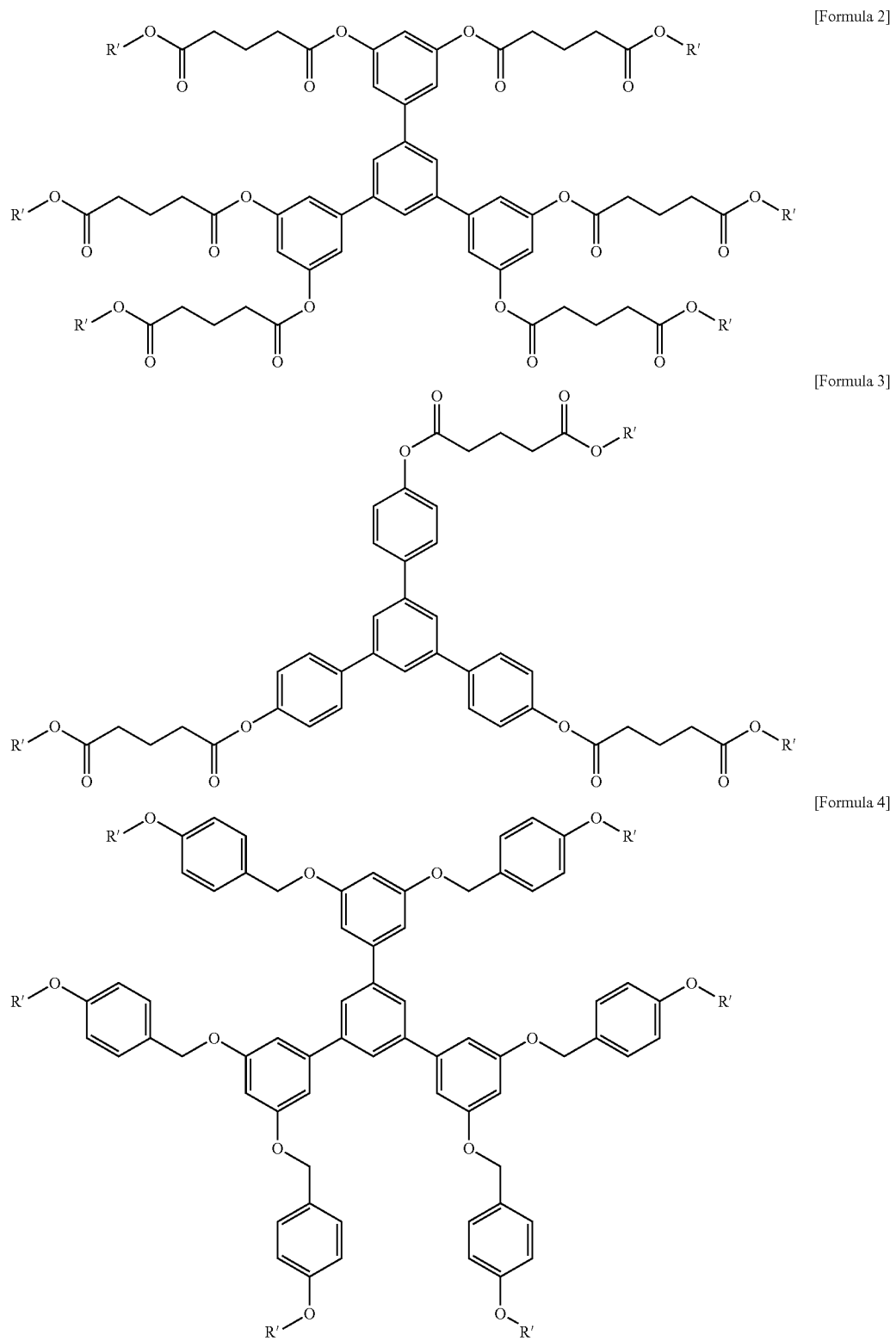
wherein, in the Formulas 2 to 4, R' is independently
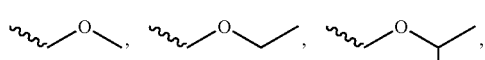
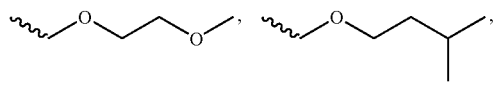

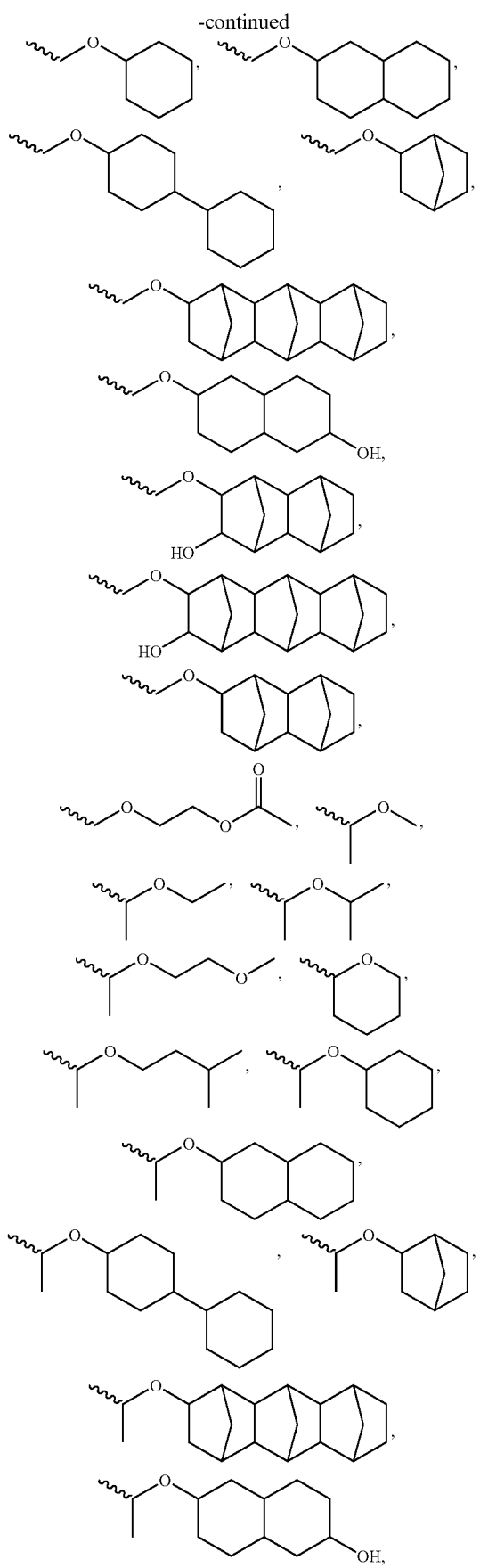
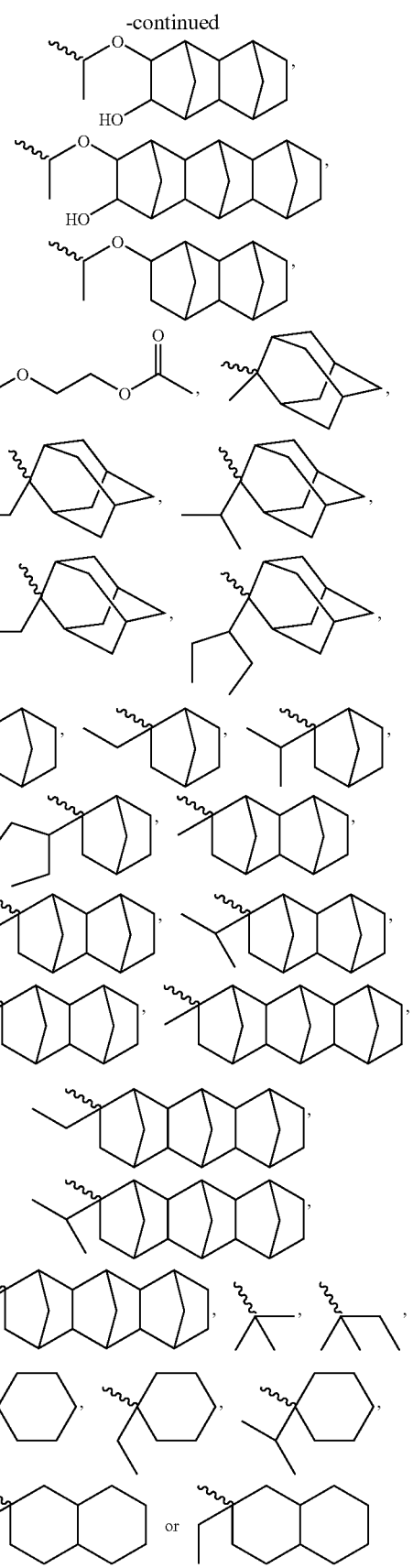
(wherein, the meandering line indicates a bonding part).

4. A photosensitive compound having a structure of the following Formula 1,

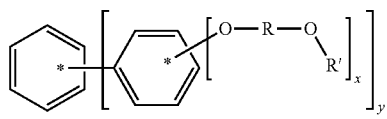
[Formula 1]

wherein, x is 1, 2, 3, 4 or 5, y is 2, 3, 4, 5 or 6, R and R' are independently a chain type, ring type aliphatic or aromatic hydrocarbon group of 1 to 30 carbon atoms, wherein the R' is an ether compound structure which includes oxygen (O) atom.

5. A photoresist composition comprising:
 1 to 85 wt % of a photosensitive compound having a structure of the following Formula 1,

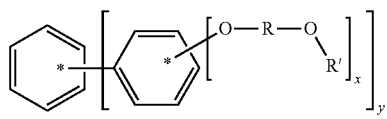
[Formula 1]

wherein, x is 1, 2, 3, 4 or 5, y is 2, 3, 4, 5 or 6, R and R' are independently a chain type or ring type of an aliphatic or aromatic hydrocarbon group of 1 to 30 carbon atoms, wherein
 (A) carbonyl (C=O) groups are positioned at both ends of R; or
 (B) R comprises a phenyl group;
 0.05 to 15 weight parts of a photo-acid generator with respect to 100 weight parts of the photosensitive compound; and
 200 to 5000 weight parts of an organic solvent with respect to 100 weight parts of the photosensitive compound.

6. The photoresist composition of claim 5, further comprising 0.01 to 10 weight parts of a base compound with respect to 100 weight parts of the photosensitive compound, wherein, the base compound is selected from a group of consisting of tri-ethylamine, tri-octylamine, tri-iso-butylamine, tri-iso-octylamine, di-ethanolamine, tri-ethanolamine and mixture thereof.

7. A method for forming a photoresist pattern, comprising the step of:
 a) coating a photoresist composition on a substrate to form a photoresist layer;
 b) exposing the photoresist layer to a light;
 c) heating the exposed photoresist layer; and
 d) developing the heated photoresist layer to form the photoresist pattern,
 wherein the photoresist composition comprises 1 to 85 wt % of a photosensitive compound having a structure of the following Formula 1,

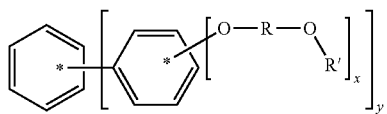
[Formula 1]

wherein, in the Formula 1, x is 1, 2, 3, 4 or 5, y is 2, 3, 4, 5 or 6, R and R' are independently a chain type or ring type of an aliphatic or aromatic hydrocarbon group of 1 to 30 carbon atoms, wherein
 (A) carbonyl (C=O) groups are positioned at both ends of R; or
 (B) R comprises a phenyl group;
 0.05 to 15 weight parts of a photo-acid generator with respect to 100 weight parts of the photosensitive compound; and
 200 to 5000 weight parts of an organic solvent with respect to 100 weight parts of the photosensitive compound.

* * * * *